(12) United States Patent
Steiner et al.

(10) Patent No.: US 11,877,070 B2
(45) Date of Patent: Jan. 16, 2024

(54) SURGICAL CAMERA SYSTEM WITH HIGH DYNAMIC RANGE AND FLUORESCENT IMAGING

(71) Applicant: ARTHREX, INC., Naples, FL (US)

(72) Inventors: Michael Dominik Steiner, Goleta, CA (US); Efrain Morales Correa, Santa Ynez, CA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 17/968,630

(22) Filed: Oct. 18, 2022

(65) Prior Publication Data

US 2023/0121217 A1 Apr. 20, 2023

Related U.S. Application Data

(60) Provisional application No. 63/257,025, filed on Oct. 18, 2021.

(51) Int. Cl.
*H04N 23/741* (2023.01)
*H04N 23/50* (2023.01)
(Continued)

(52) U.S. Cl.
CPC ............ *H04N 23/741* (2023.01); *G06T 3/40* (2013.01); *H04N 9/64* (2013.01); *H04N 23/45* (2023.01); *H04N 23/555* (2023.01); *H04N 23/84* (2023.01); *A61B 1/042* (2013.01); *A61B 1/043* (2013.01)

(58) Field of Classification Search
CPC ........ H04N 23/741; H04N 9/64; H04N 23/45; H04N 23/555; H04N 23/84; H04N 23/11; G06T 3/40; A61B 1/042; A61B 1/043; A61B 1/0005; A61B 1/045; A61B 1/00186; G02B 23/2453; G02B 23/2484; G02B 27/1013
See application file for complete search history.

(56) References Cited

U.S. PATENT DOCUMENTS 8,493,482 B2 7/2013 Cote et al.
2005/0140786 A1* 6/2005 Kaplinsky .............. H04N 23/11
348/207.1

(Continued)

OTHER PUBLICATIONS

International Search Report and The Written Opinion of the International Searching Authority, dated Feb. 9, 2023, pp. 1-14.

*Primary Examiner* — Mekonnen D Dagnew
(74) *Attorney, Agent, or Firm* — KARISH & BJORGUM, PC

(57) ABSTRACT

An endoscopic camera system having an optical assembly; a first color image sensor transmitting a first low dynamic range image; a second color image sensor transmitting a second low dynamic range image; a monochrome image sensor transmitting a monochrome image; an HDR processor coupled to the first color image sensor and the second color image sensor for receiving the first low dynamic range image and the second low dynamic range image, the HDR processor being configured to combine the first low dynamic range image and the second dynamic range image into a high dynamic range image; and a combiner coupled to the HDR processor and the monochrome image sensor, the combiner being configured to combine the high dynamic range image with the monochrome image.

19 Claims, 2 Drawing Sheets

(51) Int. Cl.
  *H04N 23/45* (2023.01)
  *H04N 23/84* (2023.01)
  *G06T 3/40* (2006.01)
  *H04N 9/64* (2023.01)
  *A61B 1/04* (2006.01)

(56) References Cited

U.S. PATENT DOCUMENTS

2013/0300887 A1* 11/2013 Ward ..................... H04N 23/54
                                                       348/218.1
2020/0134787 A1*  4/2020 Bouzaraa ................ G06T 5/003
2020/0400498 A1* 12/2020 Talbert .................. G01J 3/2823

* cited by examiner

SURGICAL CAMERA SYSTEM WITH HIGH DYNAMIC RANGE AND FLUORESCENT IMAGING

CROSS REFERENCE TO RELATED APPLICATION

This application claims priority of U.S. Provisional Patent Application No. 63/257,025, filed on Oct. 18, 2021, entitled SURGICAL CAMERA SYSTEM WITH HIGH DYNAMIC RANGE AND FLUORESCENT IMAGING, the entire contents of which are hereby incorporated herein by reference.

BACKGROUND

The present disclosure relates to devices used in endoscopic surgery and, more particularly, to an endoscopic camera system for producing images with high dynamic range and fluorescence detection.

The dynamic range of a scene may be defined as a ratio of the radiances of the brightest part of the scene and the darkest part of the scene. These radiances are detected by an imaging sensor, which has an intrinsic dynamic range. The intrinsic dynamic range can be defined as the ratio of the maximum detected scene radiance to the minimum detected scene radiance. The maximum is strongly dependent on pixel well depth and the minimum is strongly dependent on dark current noise and read noise. It is desirable to have images with greater dynamic range than the intrinsic dynamic range of most existing image sensors. In addition to visible light detection, surgeons often detect fluorescence in surgical procedures.

There exists a need for a system and method of providing high dynamic range and fluorescence images that remedies the shortcomings of the prior art.

SUMMARY

This disclosure is directed to systems and methods for combining two low dynamic range images and a fluorescence image into a single high dynamic range image. Additionally, this disclosure is directed to systems and methods for combining two low dynamic range images and a fluorescence image with a different resolution into a single high dynamic range image.

In an implementation, an endoscopic camera system has an optical assembly. A first color image sensor is in optical communication with the optical assembly, the first image sensor receiving a first exposure of visible light and transmitting a first low dynamic range image. A second color image sensor is also in optical communication with the optical assembly, the second image sensor receiving a second exposure of visible light and transmitting a second low dynamic range image, the second exposure being higher than the first exposure. A monochrome image sensor in also in optical communication with the optical assembly, the monochrome image sensor receiving an exposure of non-visible light and transmitting a monochrome image. An HDR processor is coupled to the first color image sensor and the second color image sensor for receiving the first low dynamic range image and the second low dynamic range image. The HDR processor is configured to combine the first low dynamic range image and the second dynamic range image into a high dynamic range image. A combiner is coupled to the HDR processor and the monochrome image sensor, the combiner being configured to combine the high dynamic range image with the monochrome image.

In an implementation, the first color image sensor and the second color image sensor each have a first resolution and the monochrome image sensor has a second resolution, the second resolution being lower than the first resolution. The system has a scaler coupled to the monochrome image sensor and the combiner. The scaler is configured to rescale the monochrome image to have about the same resolution as the high dynamic range image. The first color image sensor and the second color image sensor may each have a resolution of about 4K and the monochrome image sensor may have a resolution of about 2K. The color image sensors may have at least about twice the resolution of the monochrome image sensor. The color image sensors may have about four times the resolution of the monochrome image sensor. The monochrome image sensor may have a larger pixel size than the first color image sensor and the second color image sensor. Optionally, the monochrome image sensor is configured to detect near infra-red radiation.

In an implementation, an endoscopic camera system has an optical assembly. A first color image sensor is in optical communication with the optical assembly, the first image sensor receiving a first exposure of visible light and transmitting a first low dynamic range image. A second color image sensor is in optical communication with the optical assembly, the second image sensor receiving a second exposure of visible light and transmitting a second low dynamic range image, the second exposure being higher than the first exposure. A monochrome image sensor is in optical communication with the optical assembly, the monochrome image sensor receiving an exposure of non-visible light and transmitting a monochrome image.

A color receiver receives the first low dynamic range image from the first color image sensor and the second low dynamic range image from the second image sensor. A monochrome receiver receives the monochrome image from the monochrome image sensor. A processor coupled is to color receiver for receiving the first low dynamic range image and the second low dynamic range image, the processor being configured to combine the first low dynamic range image and the second dynamic range image into a high dynamic range image. A scaler is coupled to the monochrome receiver for scaling the monochrome image into a rescaled monochrome image to match a resolution of the high dynamic range image. A combiner is coupled to the processor and to the scaler, the combiner being configured to combine the high dynamic range image and the rescaled monochrome image.

In an implementation, the first color image sensor and the second color image sensor each have a resolution of about 4K and the monochrome image sensor has a resolution of about 2K. Optionally, the monochrome image sensor is configured to detect near infra-red radiation. Optionally, the color image sensors have at least about twice the resolution of the monochrome image sensor. Optionally, the color image sensors have about four times the resolution of the monochrome image sensor. Optionally, the monochrome image sensor has a larger pixel size than the first color image sensor and the second color image sensor. Optionally, the first color image sensor has a different resolution than the second color image sensor; and the system further has a color scaler coupled to at least one of the first color image sensor and the second color image sensor for scaling at least one color image to match the resolution of the color images.

This disclosure is also directed to a method of producing an image having the steps of: receiving a first color image from a first color image sensor having a first exposure; receiving a second color image from a second color image sensor having a second exposure, the second exposure being different than the first exposure; receiving a monochrome image from a monochrome image sensor configured for sensing non-visible light; combining the first color image and the second color image to make a high dynamic range image; and combining the high dynamic range image with the monochrome image. The color image sensors may have about four times the resolution of the monochrome image sensor; and the method may have the step of rescaling the monochrome image prior to combination with the high dynamic range image. In an implementation, the color image sensors have about twice the resolution of the monochrome image sensor. In an implementation, the color image sensors have a resolution of about 4K the monochrome image sensor has a resolution of about 2K. The monochrome image sensor may have a larger pixel size than the first color image sensor and the second color image sensor.

These and other features are described below.

BRIEF DESCRIPTION OF THE DRAWINGS

The features, aspects and advantages of the present disclosure will become better understood with regard to the following description, appended claims and accompanying figures wherein:

DETAILED DESCRIPTION

In the following description of the preferred implementations, reference is made to the accompanying drawings which shows by way of illustration specific implementations in which the disclosure may be practiced. It is to be understood that other implementations may be utilized, and structural and functional changes may be made without departing from the scope of this disclosure.

The present disclosure is directed to a system and method for producing high dynamic range and fluorescent images.

Figure 1:
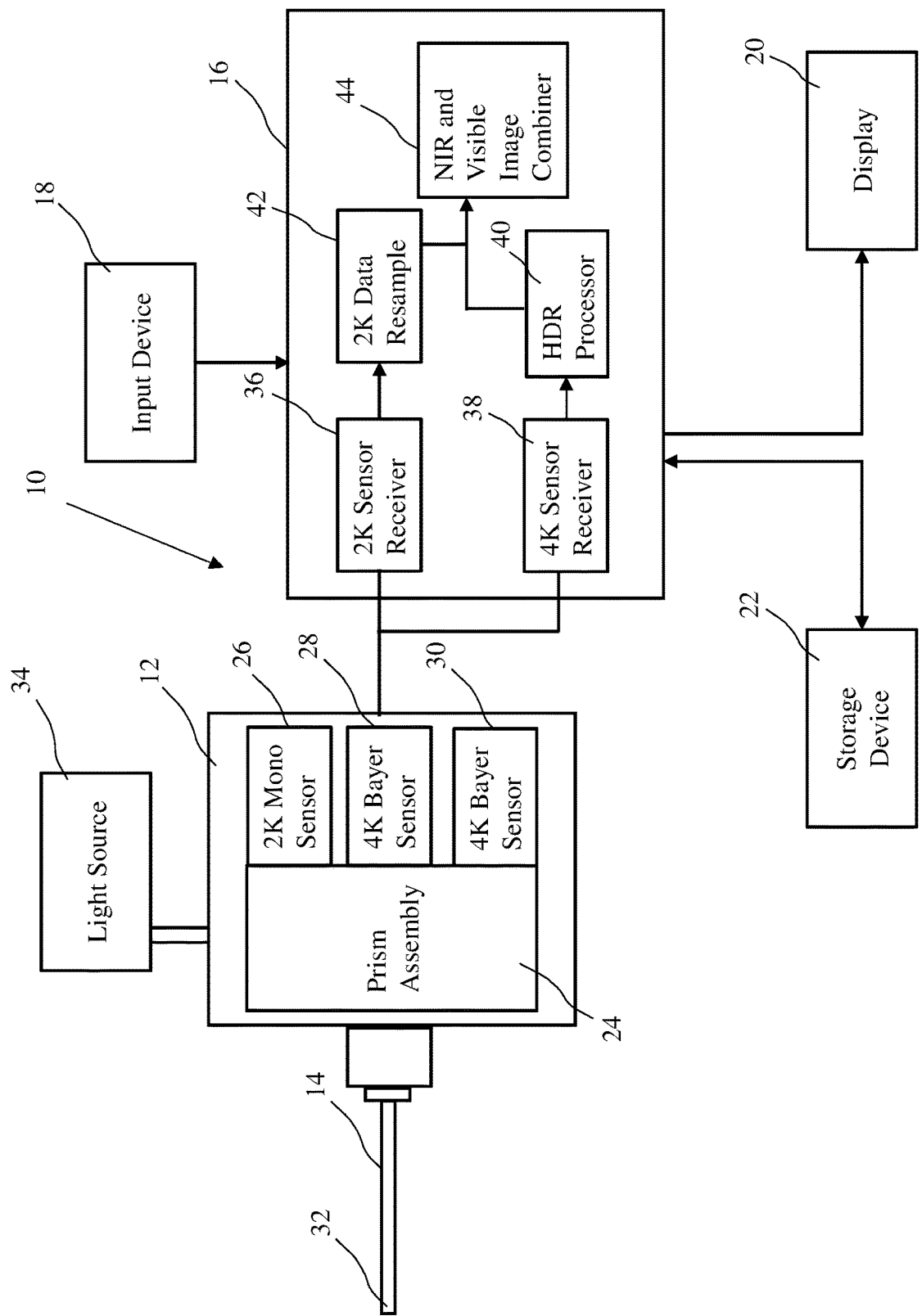
FIG. 1 is a schematic diagram of an endoscopic camera system according to an implementation.

With reference to FIG. 1, an endoscopic camera system 10 according to an implementation has a camera head 12. The camera head 12 is coupled to an endoscope 14. The camera head 12 may have an input device, such as buttons, switches, or dials. The camera head 12 is connectable to a camera controller 16 ("CCU" or "camera controller"). The camera head 12 and the camera controller 16 may be connected via wire to facilitate data transfer between the camera and the camera controller. The camera 12 and the camera controller 16 may also be wirelessly connected to facilitate data transfer, such as via IEEE 802.11b or IEEE 802.11n or ultra-wide band (UWB). The camera controller 16 may be connectable to at least one input device 18 such as a mouse, keyboard, touchpad, or touchscreen monitor. Additionally, the camera controller 20 may be connectable to a display 20 and a storage device 22, such as for storing images.

In an implementation, an optical element 24, such as a prism assembly, a monochrome image sensor 26, a first color image sensor 28 and a second color image sensor 30 are positioned inside the camera head 12. Image light is directed through the endoscope 14 and onto the prism assembly 24. In an alternative implementation, the optical element 24, the monochrome image sensor 26, the first color image sensor 28 and the second color image sensor 30 are positioned proximal to a distal end 32 of the endoscope 14. The camera head 12 may be coupled to a light source 34. In an additional implementation, the light source may be positioned inside of the camera head 12 or the endoscope 14

The light source 34 includes a lamp. The lamp may be, for example, a semiconductor light source such as laser or LED to illuminate the field of view. The light source 36 is configured to appropriately illuminate the field of view of the video camera. Further, the light generated as well as camera sensitivity may extend beyond the visible spectrum. The illumination may be intended to excite fluorescence directly in a target, or in a fluorescent substance such as indocyanine green, that is then sensed by the monochrome image sensor 26. For example, the light source 34 might produce illumination in the near infrared (NIR) range and the monochrome image sensor 26 sense the fluorescence at a longer IR wavelength. The illumination and camera sensitivity could extend from UV to NIR continuously or be composed of separate narrow bands.

Each of the monochrome image sensor 26, the first color image sensor 28 and the second color image sensor 30 may be, for example, a charge couple device (CCD) sensor or complementary metal oxide semiconductor (CMOS) sensor. The image sensors need not be identical and may have different characteristics. In a preferred implementation, the monochrome image sensor 26 is a 2k sensor used for the detection of non-visible light, such as near infra-red and infra-red light, and each of the first color image sensor 28 and the second color image sensor 30 is a 4k sensor. In additional implementations, the first color image sensor 28 and the second color image sensor 30 have different resolutions from each other. For example, in an implementation, the first color image sensor 28 is a 4k sensor, the second color image sensor 30 is 2k sensor and the monochrome image sensor 26 is a 2k sensor.

In an implementation, the first color image sensor 28 and the second image sensor 30 receive differential amounts of light. The optical element 24 may direct light so that the first color image sensor 28 receives a lower exposure, and is therefore a low exposure sensor that generates a low exposure image, and the second color image sensor 30 receives a higher exposure, and is therefore a high exposure sensor that generates a high exposure image. In an implementation, the optical element 24 directs between about 10% and about 40% of light to the first color image sensor 28 and between about 60% to about 90% of light to the second color image sensor 30. In an implementation, the optical element 24 directs between about 10% and about 20% of light to the first color image sensor 28 and between about 80% to about 90% of light to the second color image sensor 30. In an implementation, the optical element 24 directs about 10% of light to the first color image sensor 28 and about 90% of light to the second color image sensor 30. In an additional implementation, at least one of the first color image sensor 28 and the second color image sensor 30 have an optical coating to control exposure. In an additional implementation, the integration time at least one of the first color image sensor 28 and the second color image sensor 30 is independently controlled to control exposure Alternatively, the first color image sensor 28 may receive a higher exposure and the second color image sensor 30 may receive a lower exposure. Each of the first color image sensor 28 and the second color image sensor 30 generate relatively low dynamic range images. The images from both sensors are combined to create a single image with a high dynamic range. The combination to create a single image with a high dynamic range can be performed either before or after creating RGB images each from the relatively low dynamic range images. The high dynamic range image can then be tone-mapped into the range of the display. The combining and tone-mapping methods can be selected from those known in the art of creating and displaying a high dynamic range from relatively low dynamic range images.

For example, and without limitation, a method for combining two relatively low dynamic range images into a high dynamic range image may include some of the methods taught in: Paul E. Debevec and Jitendra Malik, "Recovering High Dynamic Range Radiance Maps From Photographs", ACM SISGRAPH 2008 Classes, Article 31, Pages 1-10; M. A. Robertson, S. Borman and R. L. Stevenson, "Dynamic Range Improvement Through Multiple Exposures", 1999 International Conference on Image Processing. IEEE, 1999; and Tom Mertens, Jan Kautz and Frank Van Reeth, "Exposure fusion", 15$^{th}$ Pacific Conference on Computer Graphics and Applications, IEEE 2007, the entire contents of each of which are incorporated herein by reference in their entirety.

The power consumption of each sensor is directly proportional to the number of active pixels. A 4k sensor typically has 3840×2160 active pixels and consumes about 600 mW whereas a 2k sensor typically has 1920×1080 active pixels and consumes about 300 mW or less. In endoscopic camera systems, the camera head is held by the user for extended periods of time, and, a hotter camera head (a camera head that draws significant power) may be uncomfortable and cause extra fatigue. Keeping power consumption low and camera head touch temperature low is also required to meet safety standards.

Since near infrared wavelengths are longer, the advantages of using 4k sensors with smaller pixel sizes may not improve image quality beyond a 2k image sensor. By combining two 4k color image sensors with one 2k monochrome sensor for non-visible light, the configuration optimizes for power usage while not compromising image quality.

There is also an advantage to using a 2k sensor with larger pixels. Typically, the larger the pixel size, the better the sensitivity (signal to noise ratio) of the image sensor. For endoscopic procedures where NIR signals are faint, a larger pixel size is an advantage. The combination of two 4k color sensors for visible light and one 2k sensor for non-visible light, with each sensor having the same optical format (such as ⅓"), provides an advantageous configuration for camera head power consumption, visible light image quality, and, NIR light sensitivity The camera controller 16 is preferably a programmable unit containing sufficient processing capacity to accommodate a wide range of control, user interface and image acquisition/processing functions. The camera controller 16 has a monochrome receiver 36 for receiving data from the monochrome image sensor 26. The camera controller 16 also has a color receiver 38 for receiving data from the first color sensor 28 and the second color sensor 30. An HDR processor 40 combine's images from the first color sensor 28 and the second color sensor 30 to create an HDR image.

A scaler 42 rescales the 2K image from the 2K monochrome sensor to a 4K image. In am implementation, the scaler 42 retimes the 2k sensor data rate into a 4k data rate, such as by row and column doubling, or, other interpolation method. In an implementation, the scaler 42 rescales, such as by polyphase scaling or other resampling method the resulting NIR image to match to the apparent size of the visible light image. This rescaling step is desirable, given the properties of the optical path, to meet a concurrent focus requirement (where visible light image focus and NIR image focus are at the same point using a single focus knob). A similar color scaler may be used when the first color image sensor 28 and the second color image sensor 30 have different resolutions from each other prior to combining the images from the first color image sensor and the second color image sensor.

An image combiner 44 combines the rescaled non-visible light image with the high dynamic range visible light image to generate HDR and NIR images. The resulting images may then be sent to the display 20 or stored, such as on the storage device 22. Although the monochrome receiver 36, color receiver 38, HDR processor 40, scaler 42 and image combiner 44 have been illustrated as separate elements, one or more of those elements may be combined into a single processor.

Figure 2:
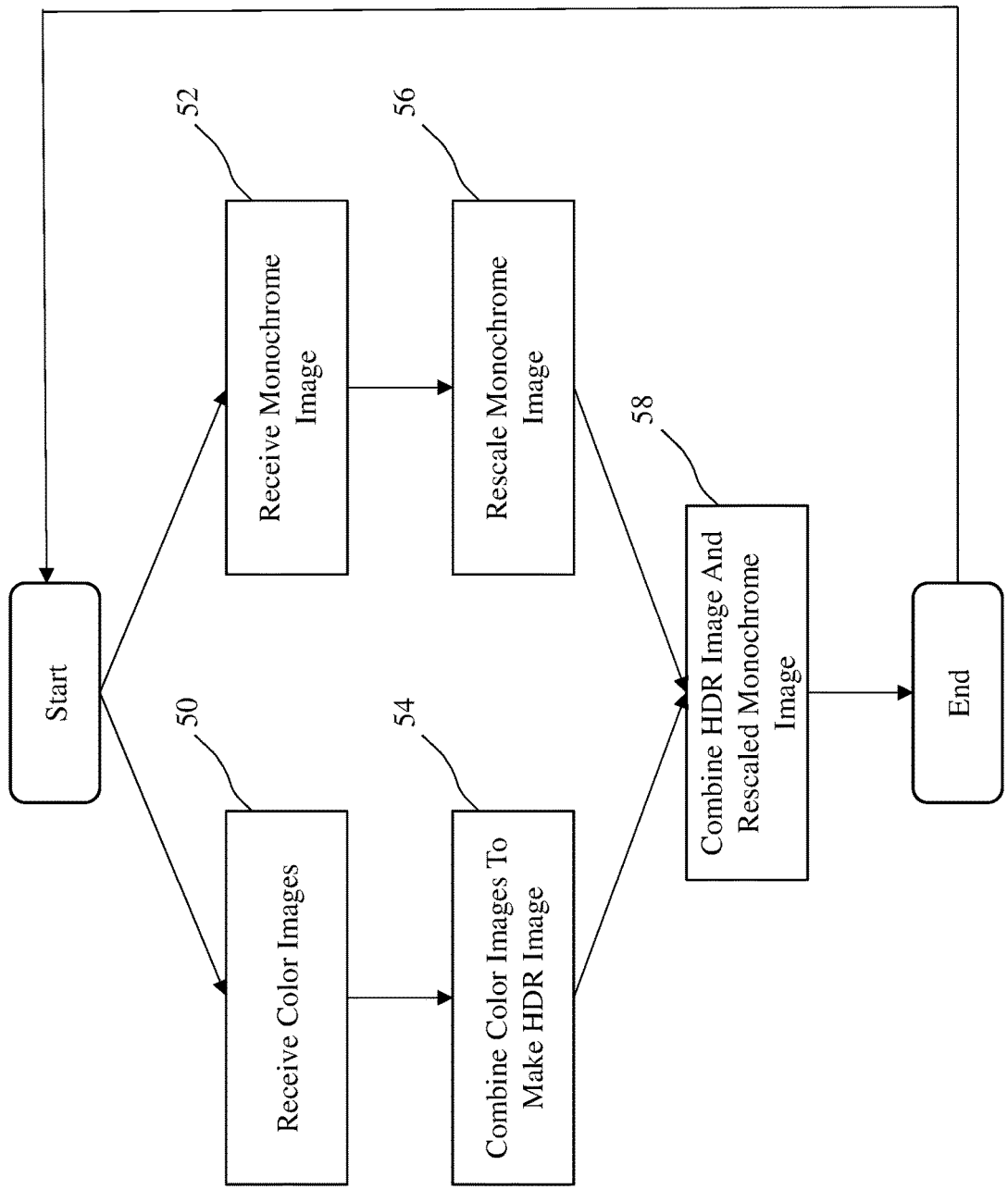
FIG. 2 is a schematic diagram of a method for making high dynamic range and fluorescence images according to an implementation.

With reference to FIG. 2, this disclosure is also directed to a method for generating high dynamic range and fluorescence images. Images are received from the first color image sensor 28 and the second color image sensor 30 in step 50. A image of detected non-visible light (such as an image of near infrared fluorescence) is received from the monochrome image sensor 26 in step 52. The images received from the first color image sensor 28 and the second color image sensor 30 are combined to make a high dynamic range image in step 54. The monochrome image is rescaled to have approximately the same resolution as the high dynamic range image in step 56. Finally, the rescaled monochrome image is combined with the high dynamic range image to generate a final image having both high dynamic range and detected non-visible light in step 58. The final image can then be displayed and saved.

There is disclosed in the above description and the drawings, a system and method for making high dynamic range and fluorescence images that fully and effectively overcomes the disadvantages associated with the prior art. However, it will be apparent that variations and modifications of the disclosed implementations may be made without departing from the principles of this disclosure. The presentation of the implementations herein is offered by way of example only and not limitation, with a true scope and spirit of the disclosure being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An endoscopic camera system comprising:
   an optical assembly;
   a first color image sensor in optical communication with the optical assembly, the first image sensor receiving a first exposure of visible light and transmitting a first low dynamic range image;
   a second color image sensor in optical communication with the optical assembly, the second image sensor receiving a second exposure of visible light and transmitting a second low dynamic range image, the second exposure being higher than the first exposure;
   a monochrome image sensor in optical communication with the optical assembly, the monochrome image sensor receiving an exposure of non-visible light and transmitting a monochrome image;
   an HDR processor coupled to the first color image sensor and the second color image sensor for receiving the first low dynamic range image and the second low dynamic range image, the HDR processor being configured to combine the first low dynamic range image and the second dynamic range image into a high dynamic range image; and a combiner coupled to the HDR processor and the monochrome image sensor, the combiner being configured to combine the high dynamic range image with the monochrome image.

2. The endoscopic camera system of claim 1 further comprising a scaler coupled to the monochrome image sensor and the combiner; wherein the first color image sensor and the second color image sensor each have a first resolution and the monochrome image sensor has a second resolution, the second resolution being lower than the first resolution; and wherein the scaler is configured to rescale the monochrome image to have about the same resolution as the high dynamic range image.

3. The endoscopic camera system of claim 1 further comprising a scaler coupled to the monochrome image sensor and the combiner; wherein the first color image sensor and the second color image sensor each have a resolution of about 4K and the monochrome image sensor has a resolution of about 2K; and wherein the scaler is configured to rescale the monochrome image to have about the same resolution as the high dynamic range image.

4. The endoscopic camera system of claim 3 wherein the monochrome image sensor is configured to detect near infra-red radiation.

5. The endoscopic camera system of claim 1 wherein the color image sensors have at least about twice the resolution of the monochrome image sensor.

6. The endoscopic camera system of claim 5 wherein the color image sensors have about four times the resolution of the monochrome image sensor.

7. The endoscopic camera system of claim 1 wherein the monochrome image sensor has a larger pixel size than the first color image sensor and the second color image sensor.

8. An endoscopic camera system comprising:
an optical assembly;
a first color image sensor in optical communication with the optical assembly, the first image sensor receiving a first exposure of visible light and transmitting a first low dynamic range image;
a second color image sensor in optical communication with the optical assembly, the second image sensor receiving a second exposure of visible light and transmitting a second low dynamic range image, the second exposure being higher than the first exposure;
a monochrome image sensor in optical communication with the optical assembly, the monochrome image sensor receiving an exposure of non-visible light and transmitting a monochrome image;
a color receiver for receiving the first low dynamic range image from the first color image sensor and the second low dynamic range image from the second image sensor;
a monochrome receiver for receiving the monochrome image from the monochrome image sensor;
a processor coupled to color receiver for receiving the first low dynamic range image and the second low dynamic range image, the processor being configured to combine the first low dynamic range image and the second dynamic range image into a high dynamic range image;
a scaler coupled to the monochrome receiver for scaling the monochrome image into a rescaled monochrome image to match a resolution of the high dynamic range image;

a combiner coupled to the processor and to the scaler, the combiner being configured to combine the high dynamic range image and the rescaled monochrome image.

9. The endoscopic camera system of claim 8 wherein the first color image sensor and the second color image sensor each have a resolution of about 4K and the monochrome image sensor has a resolution of about 2K.

10. The endoscopic camera system of claim 8 wherein the monochrome image sensor is configured to detect near infra-red radiation.

11. The endoscopic camera system of claim 8 wherein the color image sensors have at least about twice the resolution of the monochrome image sensor.

12. The endoscopic camera system of claim 8 wherein the color image sensors have about four times the resolution of the monochrome image sensor.

13. The endoscopic camera system of claim 8 wherein the monochrome image sensor has a larger pixel size than the first color image sensor and the second color image sensor.

14. The endoscopic camera system of claim 8 wherein the first color image sensor has a different resolution than the second color image sensor; and the system further comprises a color scaler coupled to at least one of the first color image sensor and the second color image sensor for scaling at least one color image to match the resolution of the color images.

15. A method of producing an image comprising the steps of:
receiving a first color image from a first color image sensor having a first exposure;
receiving a second color image from a second color image sensor having a second exposure, the second exposure being different than the first exposure;
receiving a monochrome image from a monochrome image sensor configured for sensing non-visible light;
combining the first color image and the second color image to make a high dynamic range image; and
combining the high dynamic range image with the monochrome image.

16. The method of producing an image of claim 15 wherein the color image sensors have about four times the resolution of the monochrome image sensor; and the method further comprises the step of rescaling the monochrome image prior to combination with the high dynamic range image.

17. The method of producing an image of claim 15 wherein the color image sensors have about twice the resolution of the monochrome image sensor; and the method further comprises the step of rescaling the monochrome image prior to combination with the high dynamic range image.

18. The method of producing an image of claim 15 wherein the color image sensors have a resolution of about 4K the monochrome image sensor has a resolution of about 2K; and the method further comprises the step of rescaling the monochrome image prior to combination with the high dynamic range image.

19. The method of producing an image of claim 15 wherein the monochrome image sensor has a larger pixel size than the first color image sensor and the second color image sensor.

* * * * *